US006309835B1

(12) United States Patent
Iyer et al.

(10) Patent No.: US 6,309,835 B1
(45) Date of Patent: Oct. 30, 2001

(54) METHODS FOR QUANTITATING THE EFFICACY OF ORAL CARE PRODUCTS

(75) Inventors: Lokanathan M. Iyer, Bellevue; Robert E. Akridge; James C. McInnes, both of Seattle, all of WA (US)

(73) Assignee: Koninkiijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/321,263

(22) Filed: May 27, 1999

(51) Int. Cl.[7] .............................. C12Q 1/68; C12N 1/38; A61K 7/16; C07H 21/04

(52) U.S. Cl. ......................... 435/6; 435/244; 435/252.1; 424/49; 536/24.32

(58) Field of Search ........................... 435/6, 252.1, 244; 536/24.32; 424/49

(56) References Cited

U.S. PATENT DOCUMENTS

| | | | |
|---|---|---|---|
| 4,133,875 | 1/1979 | Hillman | 424/93 |
| 4,242,812 * | 1/1981 | Randoll et al. | 434/263 |
| 4,379,135 | 4/1983 | Sasaki et al. | 436/536 |
| 4,430,324 | 2/1984 | Viccaro | 424/52 |
| 4,590,061 | 5/1986 | Southard | 424/7.1 |
| 4,913,895 | 4/1990 | Miyake et al. | 424/57 |
| 5,013,542 | 5/1991 | Hay et al. | 424/54 |
| 5,137,810 | 8/1992 | Sizemore et al. | 435/7.32 |
| 5,270,174 | 12/1993 | Rosenberg | 435/34 |
| 5,316,760 | 5/1994 | Voerman | 424/58 |
| 5,368,845 | 11/1994 | Gaffar et al. | 424/54 |
| 5,436,134 | 7/1995 | Haugland et al. | 435/34 |
| 5,472,684 | 12/1995 | Nabi et al. | 424/49 |
| 5,534,416 | 7/1996 | Millard et al. | 436/34 |
| 5,755,969 | 5/1998 | Okamoto | 210/691 |
| 5,804,395 | 9/1998 | Schade et al. | 435/7.4 |

FOREIGN PATENT DOCUMENTS

| | | |
|---|---|---|
| 0 213 059 A2 | 3/1987 | (EP) . |
| WO 91/14000 | 9/1991 | (WO) . |
| WO 9738128A1 | 10/1997 | (WO) . |

OTHER PUBLICATIONS

Molecular Probes LIVE/DEAD BacLight Bacterial viability Kits, product information sheet.*

"LIVE/DEAD BacLight Bacterial Viability Kits Appendix," Molecular Probes, Product Information Sheet (May 15, 1998).

Zambon, J.J. et al., "Rapid identification of periodontal pathogens in subgingival dental plaque," *J Periodontol* (56:32–40 1985 Nov.).

Watanabe, K. and Frommel, T.O., "Detection of Porphyromonas gingivalis in Oral Plaque Samples by Use of the Polymerase Chain Reaction," *J Dent Res* (72(6):1040–1044, Jun. 1993).

Dibart, S. et al., "Identification of bacterial species on or in crevicular epithelial cells from healthy and periodontally diseased patients using DNA–DNA hybridization," *Oral Microbiology and Immunology* (13:30–35, 1998).

(List continued on next page.)

Primary Examiner—Jeffrey Fredman
Assistant Examiner—B J Forman

(57) ABSTRACT

Methods are included for quantitating the efficacy of oral care products at dislodging cells from biofilm test surfaces or inhibit or delay the accumulation of cells on a test surface. More specifically, the inventive methods measure the effectiveness of compositions and appliances in a test environment that models biofilm surface orientations that are encountered on a tooth surface, i.e. interproximal and subgingival tooth surfaces. The use of test surfaces that are removably attachable to a tooth prosthesis allow a variety of different quantitative methods to be applied to determine the amount of cells removed or deposited in a biofilm.

35 Claims, 4 Drawing Sheets

OTHER PUBLICATIONS

Staikov, R.K. and Rudney, J.D., "Simultaneous Assay for Bacterial Aggregation, Adherence, and Killing by Saliva," *J Dent Res* (78, IADR Abst. 1890, 1999).

Guerrero, D.M. et al., "Effect of a powered toothbrush on in vitro bacterial plaque," *J Dent Res.* (78, IADR Abst. 2469, 1999).

Huntley, M.D. et al., "An in vitro assay for antimicrobial mouthrinses using ATP bioluminescence," *J Dent Res.* (78, IADR Abst. 1897, 1999).

Socransky, S.S. et al., "Checkerboard DNA–DNA Hybridization," *BioTechniques* (17:4, 1994).

Ali, R.W. et al., "Detection of identical ribotypes of *Porphyromonas gingivalis* in patients residing in the United States, Sudan, Romania and Norway," *Oral Microbiol Immunol* (12(2):106–11, Apr. 1997).

Hudson, M.C. and Curtiss III, R., "Regulation of Expression of *Streptococcus mutans* Genes Important to Virulence," *Infection and Immunity* (58(2):464–470, Feb. 1990).

Burne, R.A., "Oral Streptococci . . . Products of Their Environment," *J Dent Res* (77(3), 1988).

Clark, W.B. et al., "Comparative Estimates of Bacterial Affinities and Adsorption Sites on Hydroxyapatite Surfaces," *Infection and Immunity* (19(3):846–853, Mar. 1978).

Millward, T.A. and Wilson, M., "The effect of chlorhexidine on *Streptococcus sanguis* biofilms," *Microbios* (58:155–164, 1989).

Bonta, Y. et al., "Rapid Identification of Periodontal Pathogens in Subgingival Plaque: Comparison of Indirect Immunofluorescence Microscopy with Bacterial Culture for Detection of *Actinobacillus actinomycetemcomitans*," *J Dent Res* (64(5):793–798, May 1985).

Tanner, A. et al., "Microbiota of health, gingivitis, and initial periodontitis," *J of Clinical Periodontology* (25:85–98, 1998).

Wu–Yuan, C.D. et al., "Ability of the Sonicare Electronic Toothbrush to Generate Dynamic Fluid Activity that Removes Bacteria," *Journal of Clinic Dentistry* (5(3):89–93, 1994).

McInnes, C. et al., "Fimbria damage and removal of adherent bacteria after exposure to acoustic energy," *Oral Microbiology and Immunology* (8:277–282, 1993).

Srikantha, R. et al., "Freeze Fracture SEM Evaluation of Plaque Removal by a Sonic Toothbrush," *J Dent Res.* (75:87, 1996).

Engel, D. et al., "In Vivo Removal of Plaque Bacteria by Fluid Forces Created by a Sonic Toothbrush," *J Periodontol.* (in press 1997).

Stanford, C.M. et al., "Efficacy of the Sonicare Toothbrush Fluid Dynamic Action on Removal of Human Supragingival Plaque," *Journal of Clinic Dentistry* (8(1):10–14, 1997).

McInnes, C. et al., "Reduction in adherence of *Actinomyces viscosus* after exposure to low–frequency acoustic energy," *Oral Microbiol Immunol* (7:171–176, 1992).

Cook, G.S. et al., "Biofilm formation by *Porphyromonas gingivalis* and *Streptococcus gordonii*," *J of Periodont Res* (33:323–327, 1998).

Eifert, R. et al., "Optimization of an Hydroxyapatite Adhesion Assay for *Streptococcus sanguis*," *Infection and Immunity* (44(2):287–291, May 1984).

* cited by examiner

METHODS FOR QUANTITATING THE EFFICACY OF ORAL CARE PRODUCTS

FIELD OF THE INVENTION

The subject invention pertains to methods for quantitatively determining the efficacy with which an oral care product acts to remove cells from a biofilm or inhibits cellular deposition and growth on a surface.

BACKGROUND OF THE INVENTION

Prevention of dental plaque is important in maintaining the health of the oral cavity. Thus, new dental care compositions are constantly sought that are more effective in preventing dental plaque buildup or aid in its removal. Additionally, once cells which cause dental plaque bind to a tooth surface to form a biofilm, dental appliances must be used to remove the cells to prevent tissue irritation that leads to gingivitis, and potentially to periodontal disease or peri-implantitis.

Bacterial adherence and colonization are considered key factors in the etiology of dental plaque and biomaterial-based infections. Beachey E. H., ed. *Bacterial Adherence*, Chapman and Hall, London, 1980; Gristina A. G., *Science* 237:1588–1595, 1987. *S. mutans* has been strongly implicated as the etiological agent of dental caries (Menaker L., *The Biologic Basis of Dental Caries: An Oral Biology textbook*. Harper & Row Publishers, Hagerstow, Md., 1980) and is involved in early dental plaque formation, as is *A. naeslundii* (Socransky et al., *J Periodont Res* 12:90–106, 1977). *P. gingivalis* is a periodontopathic bacterium that has been associated with periodontal disease. van Steenbergen T. J. M., van Winkelhoff A. J., de Graaff J., In *Periodontal Disease: Pathogens & Host Immune Responses*, Hamada S., Holt S. C. McGhee J. R., Eds., Quintessence Publishing Co. Ltd., Chicago, pp. 41–52, 1991. It is now well appreciated that dental plaque results from the binding and growth of many other bacterial species on the tooth surface and that there are complex interbacterial relationships that are involved in dental plaque formation and growth. See Tanner, et al., *J. Clinical Periodontol.* 25:85–98, 1998.

Removal of dental plaque from a tooth surface usually requires direct contact between an oral care product and the plaque biofilm. There are many different types of personal dental appliances that purport to remove tooth plaque. Personal dental appliances, such as a toothbrush, rely on direct contact between the toothbrush bristles and the tooth surface to remove dental plaque. Powered toothbrushes move the bristles across the tooth to remove plaque while relying on the user to position the toothbrush about the dentition. Other dental instruments such as proxibrushes, plaque removers, and floss also rely on direct contact with the plaque accumulations to clean the tooth surface. As an alternative to direct bristle contact, oral irrigators are meant to remove plaque from teeth via fluid forces. Irrigators project a high velocity fluid jet that may be directed into areas where the bristles of a toothbrush cannot reach.

Determining the efficacy of an oral care product, whether it be an oral composition for application to the oral cavity whose purpose is to prevent the formation of plaque, or a dental appliance which is designed to remove dental plaque, can be a slow and costly process. Clinical studies are particularly expensive. Therefore, a variety of alternative test methods have been devised which allow for more time effective and less expensive determination of the efficacy of an oral care product.

Viccaro (U.S. Pat. No. 4,430,320) discloses the use of a bacterial model system to test the effectiveness of ammonium fluorometallate compounds in controlling tooth decay and plaque development. The effectiveness of the ammonium fluorometallate compounds against plaque formation was determined using an in vitro plaque development assay. Aluminum plummets pre-coated with saliva were placed into bacterial growth medium with clinical plaque samples. After a first incubation period to allow bacterial attachment and growth, the plummets were treated with the test composition and further incubated overnight in a saliva solution. On the second day the plummets were retreated with the test solution and reincubated in bacterial growth medium. The amount of bacteria growing on the surface of the plummets was quantitated by first sonicating the plummets to dislodge the bacteria into a sonication solution and then placing the solution into a spectrophotometer to determine optical density at 570 nm.

Gaffar et al., (U.S. Pat. No. 5,368,845) tested antiplaque compositions in an "artificial mouth" which pumped a constant flow of human saliva through a chamber containing two germanium plates. The test composition was pumped through the mouth for a set time period, followed by pumping a mixture of saliva (containing bacteria) and a bacterial growth medium for 24 to 48 hours. Composition efficacy was determined by performing infrared spectroscopy on the germanium plates to quantitate the amount of bacteria bound to the plates.

More commonly, the effectiveness of an antiplaque agent is determined by performing serial dilution experiments of the agent into cultures of oral bacteria to calculate the minimum inhibitory concentration, or MIC, of the agent. The MIC is the minimum concentration in micrograms per milliliter of an antimicrobial agent at which no bacterial growth is observed. At concentrations below the MIC, an antimicrobial agent is ineffective at killing or inhibiting the growth and reproduction of bacteria. At concentrations above the MIC, an antimicrobial agent is effective at killing or inhibiting the growth and reproduction of bacteria. See, for example, Nabi, et al., U.S. Pat. No. 5,472,684.

The primary drawback to using the serial dilution test on bacterial cultures to calculate a MIC of an antiplaque or antimicrobial agent is that the sensitivity of a bacterium within an in vivo multispecies plaque biofilm is different as compared to a bacterium growing in a liquid monoculture. See, for example, Millward and Wilson, *Microbios.*, 58:155–164, 1989.

Huntley, et al., (*J. Dent. Res.*, 78:343, Abst. 1897, 1999) devised an assay to measure the efficacy with which a mouth rinse kills bacteria in a biofilm rather than a planktonic liquid suspension culture. A bacterial biofilm was formed on the bottom surface of each well in a microtiter plate. Each biofilm was exposed to a mouth rinse in a time course experiment. At each assay point bacteria in the biofilm were rinsed to remove the mouth rinse and dead bacteria, and then detached from the microtiter plate well surface by sonication. The amount of alive bacteria present in the biofilm that survived the mouth rinse treatment was measured using a bioluminescence assay that measures the amount of ATP present.

One goal in the design of new dental appliances is to devise tools that are easy to use yet are effective at removing plaque from the interproximal gap regions between adjacent teeth and the subgingival region where the tooth emerges from the gum. Current appliance test methods measure the ability of a product to remove bacteria from a test biofilm surface after direct contact between the biofilm surface and the appliance (See Wu-Yuan, et al., 1994, *J. Clin. Dent.*, 3:89–93 (FIG. 2 and Table 1)), or by maintaining the appliance at a fixed distance from a biofilm surface (See Wu-Yuan, et al., 1994, *J. Clin. Dent.*, 3:89–93; Stanford et al., 1997, *J. Clin. Dent.*, 8:10–14; Smith et al, *J. Dent. Res.*, 78:414, Abst. 2469, 1999).

Effective methods are needed that allow new dental appliances to be tested to determine the efficacy with which they remove plaque bacteria and other cells from subgingival and interproximal regions. In particular, methods are needed that provide an accurate basis for comparative studies between different types of dental appliances to determine their relative efficacies in plaque removal from tooth surfaces that are hard to brush, i.e., interproximal and subgingival surfaces. In addition, methods are needed to determine the efficacy of anti-plaque formulations at preventing or inhibiting plaque development.

SUMMARY OF THE INVENTION

In one aspect, the present invention is a method for quantitating the efficacy of oral care products in the removal of dental plaque. The inventive plaque removal test method includes the following steps: 1) treating a test surface with saliva; 2) binding cells to the saliva treated test surface to form a biofilm on the test surface; 3) removing cells that are not bound to the biofilm test surface; 4) mounting the biofilm test surface in a tooth prosthesis to form a biofilm tooth prosthesis; 5) placing the biofilm tooth prosthesis into a typodont; 6) treating the biofilm tooth prosthesis with an oral care product; and 8) quantitatively determining the number of cells dislodged from the biofilm tooth prosthesis.

In yet another embodiment, the efficacy of an oral care product is determined using a method similar to that previously described except that rather than measuring the amount of cells removed from the biofilm tooth prosthesis, a quantitative method is used to determine the amount of cells that are retained in the biofilm and on the test surface after treatment of the biofilm tooth prosthesis with an oral care product.

In another aspect of the present invention a method for measuring the efficacy of an oral care product in preventing or inhibiting the formation of dental plaque is provided. The plaque inhibition test method includes the following steps: 1) treating a test surface with saliva; 2) treating the test surface with an oral care product; 3) incubating the test surface with cells under conditions conducive to the formation of a biofilm; 4) removing cells not bound to the biofilm or test surface; and 5) quantitatively determining the number of cells bound to the biofilm and test surface.

The inventive methods can be practiced using a wide variety of cell types. Many eukaryotic cell types are found in the mouth and can contribute to the formation of a biofilm. For example, an inflamed subgingival pocket surrounding a tooth contains cells mounting an immune response. In addition to bacterial and immune cells, the mouth also may contain fungal cells that contribute to biofilm formation or are present as an infective agent. The present invention provides methods for testing the efficacy of oral care products in removing or inhibiting the formation of in vitro biofilms on test surfaces that are composed of any type of eukaryotic and/or prokaryotic cells. A biofilm used in accordance with the present invention can be made using one cell type or many. More specifically, a biofilm can be formed from a combination of cells from different species, particularly cells of species selected from the large number of different bacterial species that are found in the mouth. In a preferred embodiment, the test surface is made from hydroxyapatite (HA). However, many other materials can be used as a test surface, including, but not limited to, bovine or other mammalian tooth sections, plastic, glass and metals, such as titanium, germanium and aluminum.

One aspect of the inventive methods is that the biofilm test surface can be removably positioned in a tooth prosthesis so as to more accurately model the different biofilm environments found on a natural tooth. For example, to model the removal of a cellular biofilm located in a subgingival location the biofilm test surface is mounted in a recess on the tooth prosthesis such that when the tooth prosthesis is placed into a typodont the biofilm test surface is below the artificial gum line. Similarly, to model the removal of bacteria located in an interproximal gap, the biofilm test surface is mounted on the tooth prosthesis such that the biofilm test surface is in an interproximal gap, preferably positioned so that the bristles of a tooth brush cannot make direct contact with the biofilm. In addition, a single typodont can be used simultaneously to test multiple biofilm test surfaces located on additional tooth prostheses.

A biofilm test chamber is also provided that is composed of a test chamber, which functions to retain fluid suspending the cells removed from a biofilm test surface; a typodont that is removably positioned in the test chamber and contains a plurality of tooth receiving holes; and one or more tooth prosthesis which are sized to fit snugly into the typodont tooth receiving holes. One or more of the tooth prosthesis also contain a recess sized to receive a biofilm test surface.

A number of different quantitative methods can be used to determine the number of cells either removed from a biofilm and test surface or deposited thereon. Such methods include the use of fluorescent dyes that bind specifically to cells and whose fluorescence characteristics allow live cells to be distinguished from dead cells. Further included are quantitative methods that rely upon the use of nucleic acid hybridization probes, antibody techniques, spectrophotometer readings of optical density, and other quantitative assays for cellular components such as enzymes or metabolic compounds.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
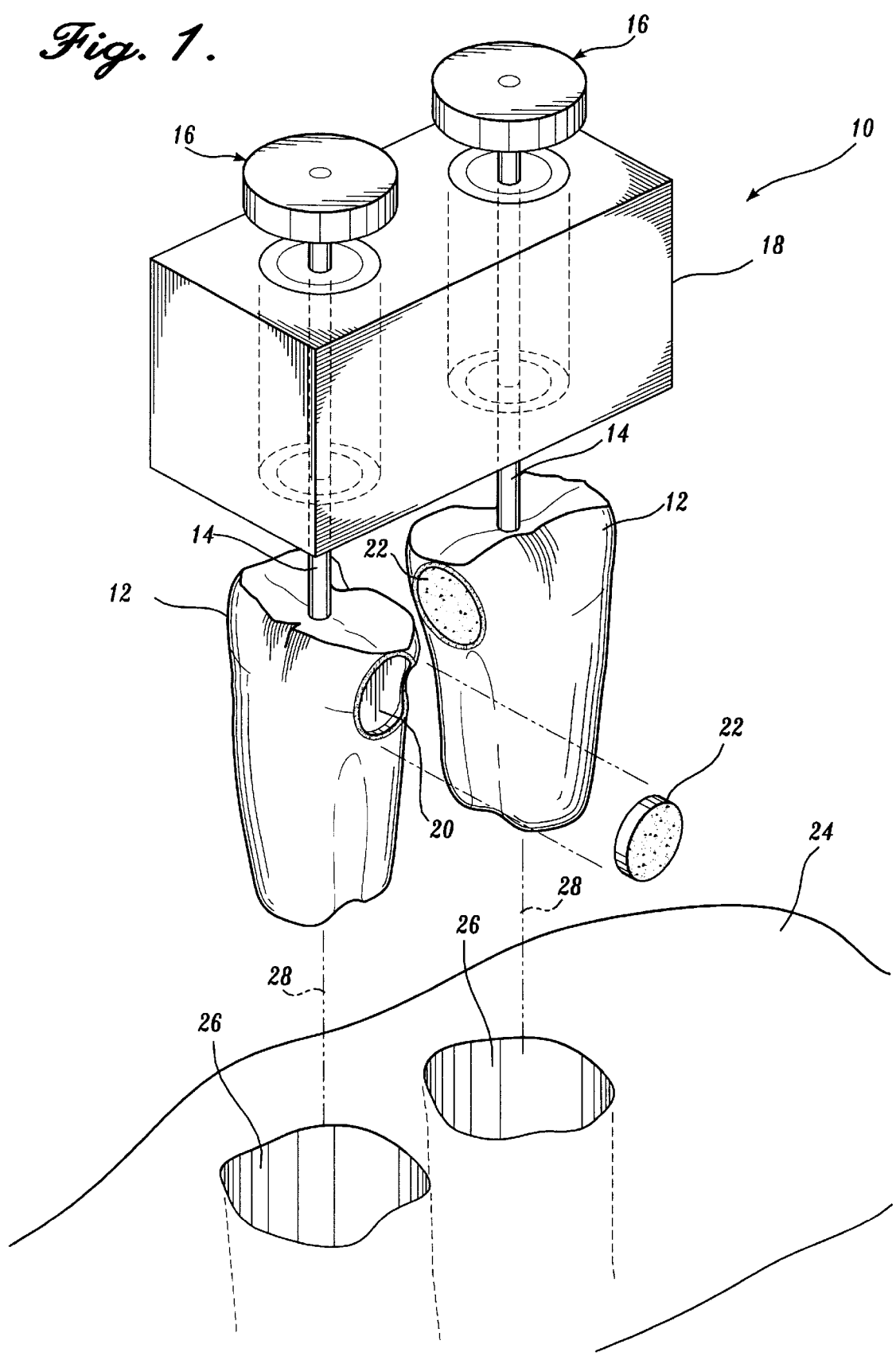
FIG. 1 is a perspective side view of a pair of tooth prostheses and a typodont.

As used herein, the following terms have the following meanings.

"Bacteria" refers to any aerobic, anaerobic, gram positive, and gram negative bacterial species.

"Biofilm" refers to the layer(s) of cells attached to a surface. A biofilm can include both alive and growing cells as well as dead cells. The biofilm can be composed of one cell type or it may be composed of two or more cell types, such as for example, a biofilm complex that is a multispecies bacterial community. A biofilm may also be composed of both eukaryotic and prokaryotic cells.

"Cell" refers to any and all eukaryotic and prokaryotic cells.

"Cell binding" refers to the attachment of cells to a test surface or to a test surface treated with saliva such that a pellicle forms upon the test surface. Cellular binding can occur directly to the test surface, the pellicle or to other cells that are already bound to the test surface or pellicle. Cells are in the bound state when they are not dislodged from a surface after multiple washes in physiological saline.

"Cellular dislodgment" refers to cells that are dislodged from a surface upon treatment with an oral care product or some other treatment such a ultrasonication, whose purpose is to remove cells from a surface.

"Gingival" refers to the gum which is the firm connective tissue that surrounds the base of the teeth. Within this application gingiva also refers to a model material, such as plastic or rubber, that is used in a typodont to model a natural gum tissue.

"Hydroxyapatite" (HA) refers to crystalline calcium phosphate.

"Interproximal gap" refers to the space that exists between to two adjacent teeth in the mouth or typodont.

"Mouth" refers to any portion of the mouth, including the tongue, gum, teeth including both supergingival and subgingival surfaces, pellicle and other surface in the mouth.

"Oral care product" refers to all articles of manufacture intended for use in the oral cavity and whose purpose is to have an effect on the health of the oral cavity. This includes instruments and appliances for removal and/or disruption of plaque or other cellular biofilms, such as proxibrushes, toothpicks, floss, tongue scrapers, plaque remover and the like, as well as formulations such as dentifrices, mouth washes and mouth rinses, oral lozenges, candy, and gums whose purpose is to prevent or inhibit biofilm formation or aid in its removal from an oral cavity surface.

"Pellicle" refers to the salivary coating that is absorbed to the surface of a tooth, any mouth surface, tooth prosthesis, typodont or test surface material. Clark et al. (1978, *Infect. Immun.* 19:846–853) provides a detailed description of the role that the pellicle plays in cellular adhesion.

"Plaque" refers to the biofilm that forms in vivo on tooth surfaces in the mouth.

"Test surface" refers to a surface made from any material that supports biofilm formation. Specific examples include, hydroxyapatite (HA), bovine or other animal tooth surfaces removed from the animal, plastic, glass and metals, such as titanium, germanium and aluminum.

"Tooth prosthesis" refers to any ex vivo structure that models any portion of a tooth.

"Typodont" refers to any ex vivo structure that models dentition containing one or more teeth.

FIG. 1 shows a tooth prostheses device 10 that has two tooth prostheses 12 that are rotationally attached to one end of pins 14. The other end of pins 14 carries a locking handle 16. Interposed between tooth prostheses 12 and handle 14 is a block 18 which serves to rotatably receive and support pins 14. The pins 14 are each reversible lockable in a position relative to the block 18 such that the tooth prostheses 12 attached to each pin 14 can no longer rotate about the axis defined by the pins 14. Each tooth prosthesis has a recess 20 sized to receive a test surface 22. In the illustrated embodiment, the recesses 20 are positioned on the tooth prostheses 12 such that when the tooth prostheses 12 are placed into a typodont 24 containing tooth receiving holes 26, the recesses 20 are in a supergingival location with respect to the typodont. In alternative embodiments of the invention the tooth prosthesis recess may be located in other locations such as, for example, in a subgingival location. Optionally, the recesses 20 are each located in the tooth prosthesis offset from the central axis 28 defined by the block attachment pin 14 to either the buccal or lingual side of the tooth prosthesis. Such an offset is desirable when testing an oral care product for its ability to remove dental plaque from an interproximal gaps without direct contact with the biofilm or test surface.

Figure 2:
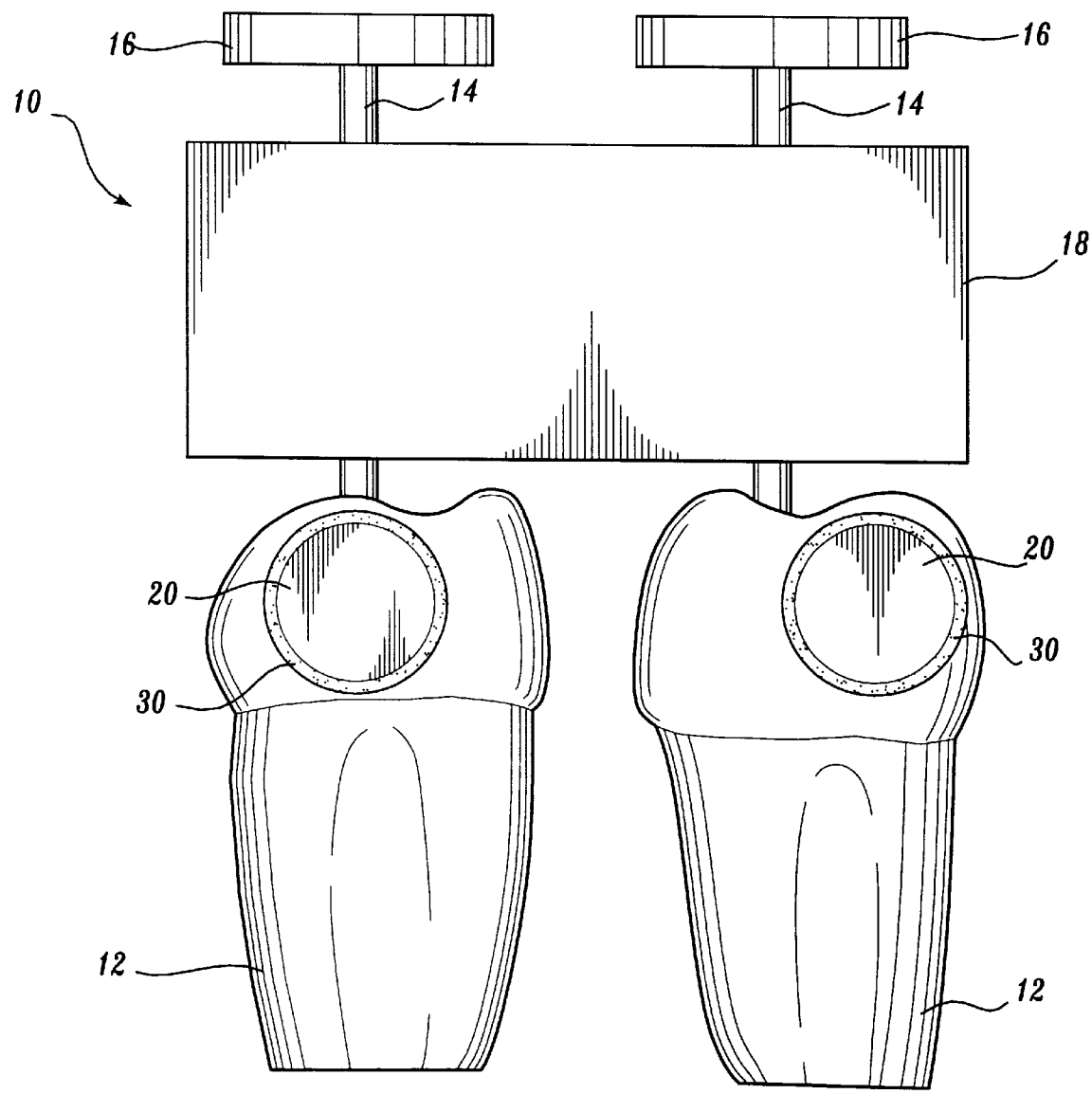
FIG. 2 is a side view of the removable tooth prostheses in an open position.

FIG. 2 shows the tooth prostheses device 10 in an open position. When the tooth prostheses 12 are in an open position the two recesses 20 are each positioned relative to the block 18 and each other in a fashion that facilitates the removable placement of a biofilm test surface 22 into each recess 20. To ensure that the test surfaces 22 are securely, but removably affixed within each recess 20, a putty like material 30, such as silicon rubber or modeling clay, is placed into each recess 20 prior to insertion of the test surface 22.

Figure 3:
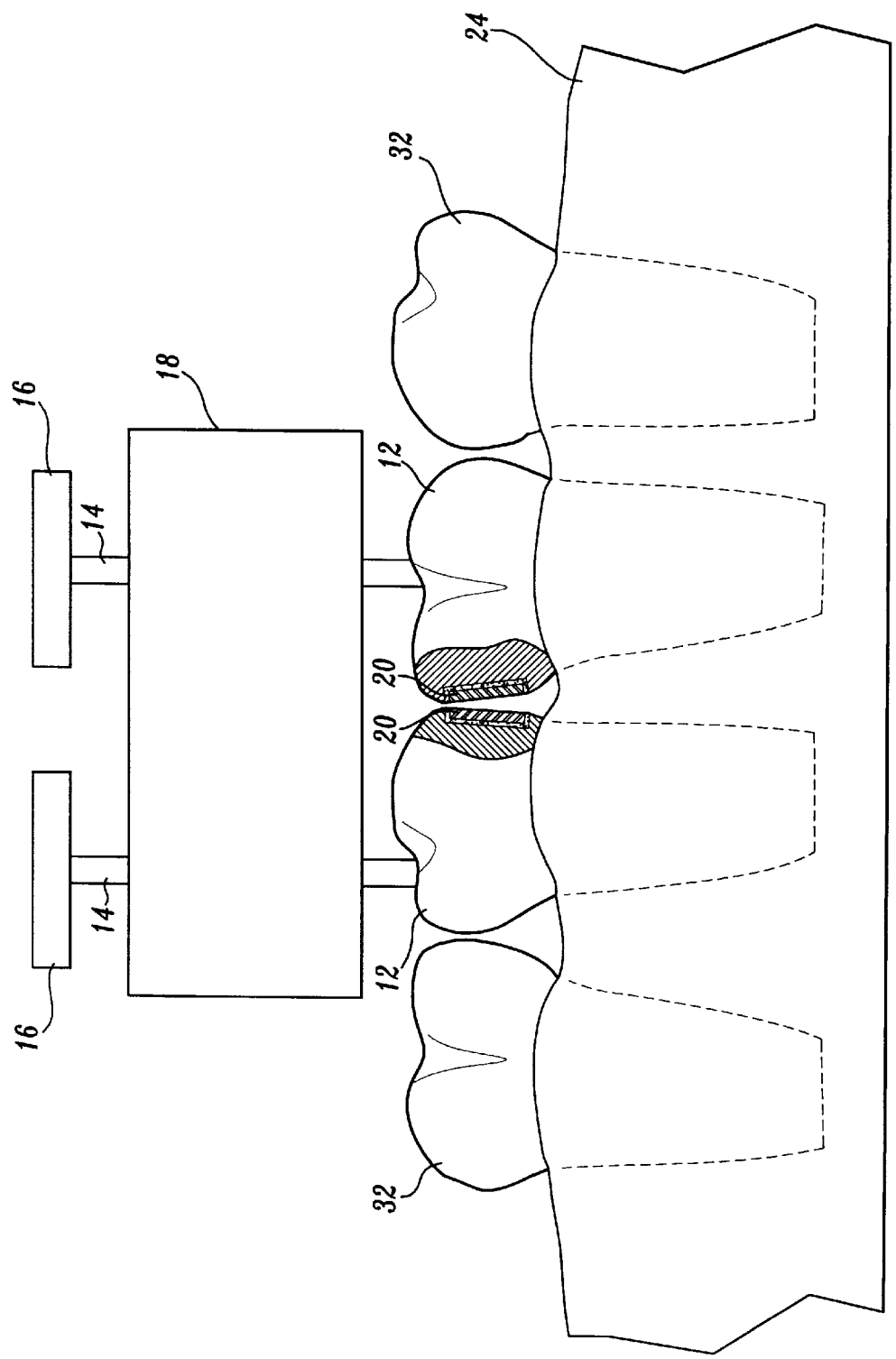
FIG. 3 is a side view of the removable tooth prostheses in a closed position and positioned in a typodont containing adjacent tooth prostheses.

To test oral care products for their efficacy at removing biofilm cells from interproximal gaps, tooth prostheses 12 are rotated to a closed position, as depicted in FIG. 3. In the illustrated embodiment, when the tooth prostheses 12 are in a closed position, the recesses 20 and inserted biofilm test surfaces 22 are positioned interproimally with respect to the tooth prostheses 12. The locking handles 16 are then placed into the locked position such that the tooth prostheses 12 are no longer rotatable. FIG. 3 also shows the tooth prostheses device 10 after placement into a typodont 24 containing two additional tooth prostheses 32 that are not rotationally affixed to the block 18. In FIG. 3, the recesses 20 are located in a supergingival position relative to the typodont 24.

Figure 4:
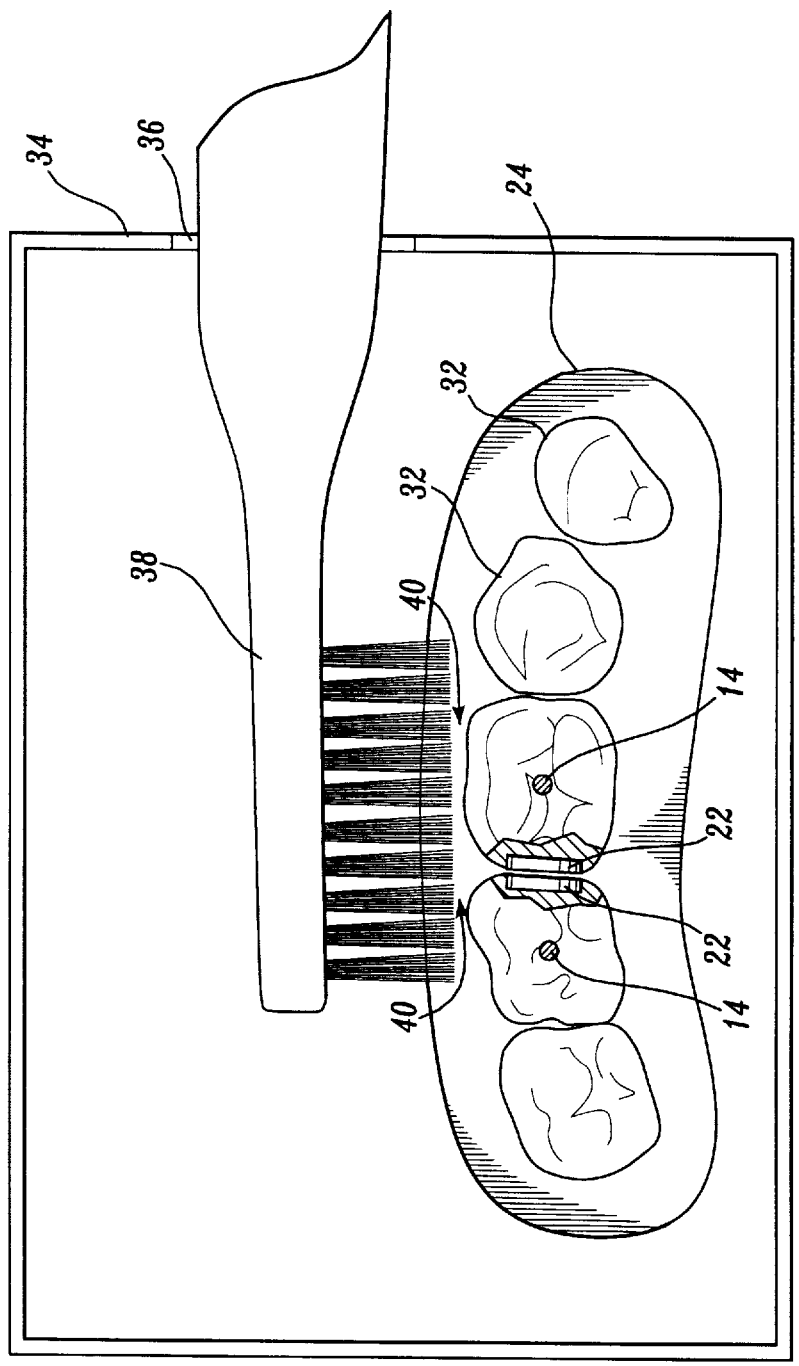
FIG. 4 is a top view of a typodont and removable tooth prostheses mounted in a collection chamber with a test dental appliance positioned to contact the buccal surface of the tooth prostheses. For clarity of viewing, the block 18 into which pins 14 are rotatably affixed is not shown.

FIG. 4 shows an overhead view of the typodont 24 and tooth prostheses 12 with attached biofilm test surfaces 22 after placement into a test chamber 34. An orifice 36 is provided in the side of the chamber to allow the insertion of a dental care product, here shown as a toothbrush 38, into the chamber 34 such that the toothbrush 38 is properly positioned to treat the buccal side 40 of the tooth prostheses 12 containing the biofilm test surfaces 22 located supergingivally in the typodont 24. Prior to treatment of the biofilm test surfaces 22 with the tooth brush 38 a lid (not shown) is placed over the test chamber 34 to prevent loss of cells removed from the biofilm test surfaces 22 by the tooth brush 38.

When a tooth brush is tested approximately 9 ml of Ringer's solution is placed into the test chamber 34 prior to treatment of the biofilm test surfaces 22 with the tooth brush 38. The fluid line of the Ringer's saliva solution is about 5 mm above the typodont 24 gum line such that it covers about ⅘ of the vertical diameter of the biofilm test surfaces 22. For each oral care product that is being tested the manufacturers' recommended tooth treatment conditions may be used to treat the biofilm test surfaces 22. After completion of the treatment period the Ringer's saliva solution contained in the test chamber 34 is collected and transferred to a 15 ml conical centriuge tube. The amount of cells dislodged from the biofilm test surfaces is determined using the quantitative methods described below.

Prior to exposure of a test surface to a cell culture to form a biofilm, the test surface is first exposed to saliva to form a pellicle. Alternatively, the test surface can be exposed simultaneously to saliva and cells. The cells can be from a purified culture collection or from cells collected from samples collected from a mouth. The biofilm that is formed on the test surface can be formed by treating the test surface with a single cell type or species. Preferably, the biofilm is formed using a more than one cell type or species found in the oral cavity. Most preferably the biofilm is formed using one of the bacterial species that are associated with dental plaque, gingivitis and interproximal and buccal periodontitis as described in Table 3 in Tanner et al. (*Clinical Peridontology*, 25:85–98, 1998), which is herein incorporated by reference. Such oral bacterial species include: *Actinomyces gerencseriae, Actinomyces israelii, Actinomyces naeslundli, Actinomyces odontolyticus, Actinomyces viscosus, Bacteroides forsythus, Bacteroides gingivalis, Capnocytophaga gingivalis, Campylobacter gracilis, Campylobacter rectus, Capnocytophaga ochraceu, Capnocytophaga sputigena, Eikenella corrodens, Eubacterium brach, Eubacterium lentum, Eubacterium nodation, Fusobacterium alocis, Fusobacterium nucleatum ss. fusiforme, Gemella morbillorum, Haemophilus aphrophilus, Lactobacillus uli, Peptostreptococcus micros, Porphyromonas gingivalis, Prevotella intermedia, Prevotella nigrescens, Rothia dentocariosa, Selenomonas flueggeii, Selenomonas noxia, Selenomonas spuhigena, Streptococcus anginosus, Streptococcus crista, Streptococcus gordoniz, Streptococcus oralis, Streptococcus intermedius, Streptococcus mills, Streptococcus mutans, Streptococcus salivarius, Streptococcus sanguis, Treponema denticola* and *Veillonella parvula*. In addition, the biofilm can also be formed by treating the test surface with two or more additional cell types to form a multicellular biofilm that is more reflective of the biofilm composition found on naturally occurring dental plaque.

One aspect of the present invention is that the biofilm test surface can be removably positioned in a tooth prosthesis so as to more accurately model the different biofilm environments found on a natural tooth. For example, to model the removal of bacteria located in a subgingival location the biofilm test surface is located in a recess on the tooth prosthesis such that when the tooth prosthesis is mounted in a typodont the biofilm test surface is below the artificial gum line. Similarly, to model the removal of bacteria located in an interproximal gap, the biofilm test surface is mounted on the tooth prosthesis such that the biofilm is in an interproximal gap, preferably positioned so that the bristles of a tooth brush cannot make direct contact with the biofilm. In addition, a single typodont can be used to simultaneous test multiple biofilm test surfaces located on additional tooth prostheses.

The typodont is placed into any type of chamber that allows reproducible recovery of cells that has been dislodged from the biofilm test surface due to treatment with an oral care product. The collection chamber is preferably designed to accommodate the insertion and removal of the typodont and affords an access orifice into which an oral care product is inserted such that its biofilm removal function is operative.

The amount of cells dislodged from the biofilm test surface by an oral care product is quantitatively determined using one of several possible methods. Alternatively, the amount of cells that are remaining in the biofilm after treatment of the biofilm by an oral care product can be quantitatively determined by several possible methods. One simple method of determining the amount of cells in an aqueous sample is to place the cellular sample in a spectrophotometer and measure the optical density of the sample using a suitable wave length. See, for example, Viccaro, U.S. Pat. No. 4,430,320.

More sensitive assays for determining the amount of cells in a sample are obtained by using fluorogenic dyes or antibodies that are specific to cells in the biofilm. One advantage to these techniques is that the amount of cells bound to the test surface can be quantitatively determined either by first removing bound cells, by for example a sonication treatment which quantitatively removes cells from a test surface, or the amount of cells in a biofilm can be directly determined by measuring the amount of fluorescence emitted from the test surface. A wide variety of dyes and antibody systems are well known in the microbial cell biology arts. Many such reagents are commercially available from Molecular Probes, Inc. (Eugene, Oreg.). The catalog and handbook published by Molecular Probes contains an extensive discussion of fluorescent dyes and antibody probes and provides methods and references that discuss how these reagents can be used to detect and quantitatively determine the amount of bacteria and eukaryotic cells contained in a sample. See R. P. Haugland, *Handbook of Fluorescent Probes and Research Chemicals*, 6th Edition, 1996, which reference is herein included in its entirety by reference. Table 1 lists fluorescent dyes that can be used to stain bacteria and eukaryotic cells and denotes which dyes can detect whether the cell is live or dead.

TABLE 1

| Stain/Dye | Live/Dead Indicator |
|---|---|
| 4',6-diamindino-2-phenylindole (DAPI) | live/dead |
| Sytox Green ™ | dead* |
| Sytox Blue ™ | dead* |
| Hoechst 33342 | live* |
| Hoechst 33258 (BIS-BENZIMIDE) | live* |
| TO-PRO-1 ™ | dead |
| TO-PRO-3 ™ | dead |
| TO-PRO-5 ™ | dead |
| TOTO-1 ™ | dead |
| TOTO-3 ™ | dead |
| YO-PRO-1 ™ | dead |
| YOPRO-3 ™ | dead |
| YOYO-1 ™ | dead |
| YOYO-3 ™ | dead |
| BOBO-1 ™ | dead |
| BOBO-3 ™ | dead |
| PB-PRO-1 ™ | dead |
| BO-PRO-3 ™ | dead |
| Ethidium bromide | dead |
| Ethidium Homodimer-2 | dead |
| POPO-1 ™ | dead |
| POPO-3 ™ | dead |
| PO-PRO-1 ™ | dead |
| PO-PRO-3 ™ | dead |
| Propidium Iodide | dead |
| SYTO 11, 12, 13, 14, 15, 16, 20, 21, 22, 23, 24, 25 ™ | live |
| SYTO 17 ™ | live/dead* |
| SYTO 9 ™ | live* |
| SYTO 10 ™ | live |
| SYBR 14 ™ | live |
| FUN 1 ™ | live (fungi) |
| DEAD RED ™ | dead |
| Wheat Germ Agglutinin-fluorescently labeled (e.g., Texas Red) | gram+ |

*= dyes that have been used specifically for staining bacteria. Other dyes have been used for staining eukaryotic cells, but could also be used to stain bacteria or fungi.
™= trademark of Molecular Probes, Inc. All the listed dyes are commercially available from Molecular Probes, Inc. (Eugene, OR).

Additional publications that disclose the use of fluorescent dye methods to quantitatively detect prokaryotic and eukaryotic cells in a sample are U.S. Pat. Nos. 5,436,134 and 5,534,416. Zambon, et al., (*J. Periodontol*, 56:32–40, 1985)

and Bonta, et. al., (*J. Dent. Res.* 64:793–798, 1985) both describe the use of fluorescently labeled antibodies to detect oral cavity bacteria in samples. U.S. Pat. No. 5,137,810 describes a wheat germ agglutinin kit that utilizes lectins that bind specifically to bacteria in a sample in order to detect and quantitate the presence of bacteria.

Alternatively, cellular concentration in a sample can be determined using an assay specific to a compound known to be present in the biofilm cells. See for example, Huntley et al., 1999, (*J. Dent. Res.*, 78:343, Abst. 1897, 1999). In addition, a number of quantitative methods can be used to determine the amount of cells in a sample after first extracting nucleic acid from the biofilm cells. More specifically, two kinds of nucleic acid techniques can be used to detect and quantitate the amount of cells that are present in a sample:

1) Nucleic acid hybridization methods using oligonucleotide probes or total DNA probes that hybridize specifically with nucleic acids extracted from biofilm cells. See Skobe et al., *Oral Microbiol. Immunol.* 13:30–35, 1998; Tanner et al., *J. Clinical Periodontology* 25:85–98, 1998; Ali et al., *Oral Microbiol Immunol.* 12:106–111, 1997.

2) Oligonucleotide primers that are used in the polymerase chain reaction (PCR) to quantitatively amplify specific DNA fragments from the nucleic acid samples of cells. See Watanabe and Frommel, *J. Dent. Res.* 72:1040–1044, 1993. A wide variety of PCR methods are described in Higuchi (*PCR Technology: Principles and Applications for DNA Amplification*, Stockton Press, New York, p. 61–70, 1989), which reference is herein included in its entirety by reference.

The following nonlmiting examples illustrate examples of the inventive methods and the use of them to determine the efficacy with which oral care products either limit cellular binding to a test surface or are effective in removal of cells from a biofilm.

EXAMPLE 1

Quantitative Measurement of Bacterial Removal from a Hydroxyapatite Biofilm

Preparation of the Hydroxyapatite Disc

Dense Hydroxyapatite (HA) discs (5 mm diameter×2 mm; Clarkson Chromatography Products, Inc.; South Williamsport, Pa.) were placed in Ringer's irrigation solution (Baxter Healthcare Corp., Deerfield, Ill.) for 30 minutes. All discs were then transferred to a petri dish (100×15 mm, VWR) containing enough 10% saliva solution (see below) to completely cover the tops of all discs while shaking on an orbital shaker. The discs were kept on the shaker at the lowest possible speed overnight at room temperature. The next day all discs were transferred to 12 well flat bottom plates. While transferring, excess saliva solution was removed from the discs by flicking each disc while being held between sterile forceps. The discs are maintained throughout the procedure with the saliva-exposed surface facing upward.

Saliva Solution

Saliva from one individual (5 ml) was collected in a 50 ml polystyrene conical tube (Falcon No. 2074) to which was added 45 ml of sterile Ringer's Irrigation solution (Baxter No. 2F7164). The mixture was then vortexed, and passed through a 115 ml Nalgene filter unit (0.2 micron) containing a pre-filter to remove large particles. The sterilized 10% saliva solution was then transferred, under sterile conditions, to a 50 ml sterile conical tube and was stored at 4° C. until needed. Saliva solutions were always used within 48 hours of collection. In addition, a given saliva solution was used to coat only one group of HA discs.

Treatment of HA Discs with Bacteria:

Once the HA discs were transferred to each well (five discs/well), 1 ml of a 2% sucrose+Trypticase Soy Broth (30 g/l, Trypticase Soy Broth; Becton Dickinson; BBL+1 g/l, Yeast Technical Extract; Difco=TSB) was added to each well along with 1.0 ml of log phase *Streptococcus mutans* (See Table 2). The plates were placed on an orbital shaker for 10 minutes (100 RPM) at room temperature. The plates were then transferred to a 37° C. incubator+5% $CO_2$/air for eight hours. After incubating, discs were placed on a shaker for 10 minutes (100 RPM), transferred to a new 12 well plate (5 discs/well) containing 1 ml of TSB-sucrose/well, and followed by the addition of 1 ml of a log phase culture of *Streptococcus sanguis* (See Table 2). The plates were placed on orbital shaker for five minutes at room temperature, and then incubated overnight at 37° C. incubator+5% $CO_2$/air. The next day, discs were gently shaken with forceps to remove excess bacteria, and placed in a 12 well plate containing diluted Badight Viability Dye (see below) for two hours at room temperature in dark.

Fluorescent Labeling of Biofilm Discs

A sterile Ringer's solution containing 2% sucrose was added (1.5 ml) to each well of a 12 well plate. The LIVE/DEAD BacLight Bacterial Viability Kit (Molecular Probes, Eugene Oreg.) consists of two dyes, both of which are solid at 4° C. and were warmed to room temperature. After letting the dyes become liquid, 3 µl of each stain was then added to each well, and mixed by pipetting the diluted dye up and down. The bacterial-laden HA discs were placed into the dye solution for two hours at room temperature in the dark until needed.

Bacterial Cultures

Frozen cultures were made using log phase bacterial cultures. The bacterial cultures were added to an equal volume of a 20% glycerol solution, and rapidly placed in the vapor phase of liquid nitrogen. When thawing frozen bacterial cultures, each vial was removed from freezer and warmed in hands. A 50 µl inoculum of bacteria was then added to 5 ml of TSB, and cultured for 24 hours at 37° C.+5% $CO_2$/air. Subcultures were made everyday by transferring 50 µl of bacteria to 5 ml of 37° C. TSB. Only log phase bacterial cultures made the day before were used for producing biofilm-HA discs. Bacteria were only maintained for two weeks before a new frozen culture was thawed. Table 2 sets forth specific bacterial species, along with the growth media and incubation condition for that microorganism.

TABLE 2

Microorganisms/Growth Media/Incubation Conditions

| Microorganism | ATCC No. | Growth Media | Incubation Conditions |
|---|---|---|---|
| *Campylobacter rectus* | 33238 | CR media[4] | 48 hrs/37° C./anaerobic |
| *Actinomyces viscosus* (AV) | 19246 | TSB[1] | 48 hrs/37° C./aerobic |
| *Fusobacterium nucleatum* (FN) | 10933 | FN media[3] | 48 hrs/37° C./anaerobic |
| *Porphyromonas gingivalis* (PG) | 33277 | PG media[2] | 48 hrs/37° C./anaerobic |
| *Streptococcus mutans* (SM) | 25175 | TSB[1] | 48 hrs/37° C./aerobic |

TABLE 2-continued

Microorganisms/Growth Media/Incubation Conditions

| Microorganism | ATCC No. | Growth Media | Incubation Conditions |
|---|---|---|---|
| *Streptococcus sanguis* (SS) | 49295 | TSB[1] | 48 hrs/37° C./ aerobic |

[1]Tryptic Soy Broth 3.0% wt. to vol., yeast extract 0.1%, and 999 milliliters distilled water.
[2]Tryptic Soy Broth 3.0% wt. to vol., yeast extract 0.5%, L-cystein 0.05%, Hemin 0.0005%, Menadione 0.00002%, and 990 milliliters distilled water.
[3]Tryptic Soy Broth 3.0% wt. to vol., yeast extract 0.5%, Peptone 1.0%, L-cystein extract, Hemin 0.0005%, Menadione 0.00002%, and 990 milliliters distilled water.
[4]Brain Heart Infusion Broth 0.74% wt. to vol., yeast extract 0.01%, sodium formate 0.2%, sodium fumerate 0.03%, hemin 0.005% and 990 milliliters distilled water.

Treatment of Hydroxyapatite Biofilms with An Oral Care Product

As previously depicted in FIGS. 1–4, the HA test surfaces that have been treated with bacteria to create a biofilm are placed into a recess in a tooth prosthesis. The tooth prosthesis is placed into a typodont which is in turn mounted in a test chamber. The test chamber is configured to contain the bacteria that are dislodged from the biofilm and HA surfaces due to treatment with an oral care product. In this example a manual toothbrush and an automatic toothbrush were tested for their efficacy at removing a biofilm from HA test surfaces located in an interproximal gap. The arrangement of the HA test surface, tooth prostheses, typodont, test chamber and toothbrush was as depicted in FIGS. 1–4.

Prior to treatment of the biofilm test surfaces with the test toothbrush approximately 9 ml of Ringer's saliva solution (66.6% Ringers solution, 33% Saliva Substitute, Roxane Laboratories, Inc. Columbus, Ohio) was placed into the test chamber. The fluid line of the Ringer's saliva solution was about 5 mm above the typodont gum line such that it covered about $\frac{4}{5}$ of the vertical diameter of each of the biofilm test surfaces. Each toothbrush was tested using the manufacturers' recommended brushing conditions regarding the angle with which the toothbrush bristles make contact with the teeth and the length of brushing time. After completion of the treatment period the fluid contained in the test chamber was collected and transferred to a 15 ml conical centrifuge tube. The amount of bacteria dislodged from the biofilm and HA surfaces was determined using the following methods.

Processing of Bacterial Samples after Appliance Treatment

All bacteria sample tubes were vortexed to resuspend any settled bacteria In other cases where the viscosity of the solution was thick, samples were reduced to a 4 ml volume. 10 ml of Ringer's solution was then added to each tube and vortexed. All specimens were then reduced to an 8 ml volume. Tubes were centrifuged at 1,750 RFC for 15 minutes at room temperature. After centrifugation, the volume of each tube was reduced to 0.5 ml by carefully pipetting out the majority of the solution. The sample tubes were manually agitated to resuspend the pelleted bacteria. The bacterial suspension was then transferred to a microfuge tube (1.5 ml), sonicated for three seconds (power level 3) with a Sonic Dismembrator 60 (Fisher Scientific, Pittsburgh, Pa.) using an ultrasonic converter microprobe. A 150 μl sample of each sonicated bacteria was transferred to a micro-sert glass cuvette (Fisher Scientific, Catalog No. 03-375-ID), and placed in Turner fluorometer for quantitation of the amount of fluorescence using the excitation and emission wavelengths recommended by the Molecular Probes, the manufacturer of the fluorescent dyes.

Table 3 presents the data collected from an experiment comparing the efficacy of an automatic tooth brush to a manual tooth brush.

TABLE 3

Relative Fluorescent Units (RFU) of Cells Removed from Biofilm Test Surface Following Brushing in Typodont

|  | Electric Toothbrush | Manual Toothbrush | No Brush (Control) |
|---|---|---|---|
| RFU per disc | 490 | 74 | 62 |
|  | 569 | 75 | 69 |
|  | 1482 | 96 | 66 |
|  | 1260 | 97 | 60 |
|  | 1386 | 77 | 69 |
| Mean | 1037 | 83.8 | 65 |
| Standard Deviation | 471 | 11.6 | 4 |

The results presented in Table 3 demonstrate that the inventive method is effective at quantitatively measuring the amount of cells removed from a biofilm test surce. In this particular set of experiments the electric toothbrush was over ten times more effective at removing bacteria from biofilm test surfaces located in an interproximal location in a typodont than the manual toothbrush. Thus, using the inventive methods the relative efficacy with which any oral care product removes cellular biofilms from a test surface can be quantitatively determined. High fluorescence emission in a sample is equated with a high level of cell removal from the biofilm test surface. In contrast, a less effective oral care product shows a low amount of fluorescence in the removed cell sample as compared to an effective oral care product.

EXAMPLE 2

Quantitative Measurement of Bacterial Adherence to a Hydroxyapatite Biofilm

Many oral care products are designed to inhibit cell attachment and growth on mouth surfaces. This example describes a method in accordance with the present invention for measuring the efficacy of oral care products in preventing plaque buildup or otherwise limiting cell attachment and growth in biofilms.

The growth of bacteria was as described in Example 1. Bacteria were diluted to an O.D. of 0.4 using a spectrophotometer set at 550 nm prior to use in the adherence assay. HA discs (5 mm diameter×2 mm) preincubated in saliva and stored overnight as described in Example 1 were transferred to a 12 well tissue culture plate (3 discs/well). Each well contained either a control formulation or a different dilution of a test formulation. Test formulations were diluted 2 parts formulation to 1 part Ringer's saliva solution (66.6% Ringer's solution, 33% Saliva Substitute, Roxane Laboratories, Inc. Columbus, Ohio) prior to transfer to the tissue culture plate well. The discs were allowed to incubate in their respective solutions (test formulations and control formulations) for 3 minutes at room temperature. At the end of the incubation, each HA disc was dipped into Ringer's solution and quickly transferred to a new tissue culture plate well containing 1 ml of TSB and 2% sucrose. After all discs were transferred, 500 μl of log phase *Streptococcus mutans* was added to each well (except for wells meant as no bacteria controls). The disc and bacteria were gently mixed and then incubated at 37° C. for 3 hours.

When using fluorescent dyes to quantitate the amount of cells present in a liquid or test surface sample it is important to include a variety of control samples. The data from the control samples allows systematic corrections to made to the data collected from the actual test samples. For example, if the test formulation or HA discs contain a fluorescent compound this needs to be determined and subtracted from the raw fluorescent data. In addition, a zero bacterial adherence control sample is included by incubating a set of HA discs with 0.5–2% sodium lauryl sulfate which prevents bacterial adherence to the HA discs. Lastly, control samples are always included which define the 100% cellular adherence baseline for bacterial binding to the HA disc. The 100% adherence control is made by incubating HA discs with bacteria in the absence of any test formulation. The efficacy of a test formulation is determined by comparison of bacterial binding in the presence of the test formulation to the 100% adherence control. Highly effective formulations exhibit a low level of bacterial adherence as compared to the 100% adherence control and conversely, less effective test formulations exhibit a high level of bacterial binding.

Methods for Measuring Bacterial Adherence

In this embodiment of the invention bacterial adherence to a HA disc is measured by first treating the HA disc with a test formulation, incubating the treated disc with bacterial for a fixed period of time, rinsing the HA disc in saline to remove excess bacteria that have not adhered to the disc, and sonicating the disc to quantitatively remove the bacteria which comprised the biofilm on the HA disc. The bacteria released from the HA test surface by the sonication are collected and counted using fluorescent dyes that bind to the bacteria. The number of bacteria that were in the biofilm formed on the HA disc treated with a test formulation is then determined by measuring the amount of flourescence.

In this embodiment of the present invention, the HA discs were incubated with the bacteria for 3 hours. After the incubation excess bacteria were removed from the HA discs by placing groups of three discs into a common microfuge tube with 1 ml of Ringer's solution. Each microfuge tube was vortexed for 10 seconds and sonicated for 30 seconds in a Sonic Dismembrator 60 sonicator (Fisher Scientific, Pittsburgh, Pa.) at maximum power. The Ringer's solution was then pipetted up and down to suspend the dislodged bacteria. The HA discs were then inspected under a microscope to ensure that substantial all of the adhering bacteria were dislodged by the sonication treatment. If necessary an additional sonication treatment was used to ensure quantitative removal of bacteria from the disc surface. The discs were then removed from the microfuge tube and the bacteria suspended in the Ringer's solution were pelleted by centrifugation for 15 minutes at 6,000×g. The resulting supernatant was removed from the microfuge tube. The bacterial pellet in each tube was resuspended by mechanically shaking the tube and by adding 1 ml of SYTOX Green™/DAPI dye solutions (Molecular Probes, Inc., Eugene, Oreg.) made by mixing 2 µl of SYTOX Green™, 4 µl of DAPI per 1 ml of Ringer's solution. The bacteria resuspended in the dye solution were kept in the dark for 20 minutes and then centrifuged for 15 minutes at 6,000×g. The resulting supernatant was removed and the dyed bacterial pellet resuspended in 500 µl of Ringer's solution. The dyed bacteria were then placed into a black plastic/clear bottom 96 well flat bottom plate (Corning CoStar Corp., Cambridge, Mass., catalog number 3603) in duplicate.

Alternatively, the number of bacteria adhering to the test surface can be determined by dyeing the bacteria while bound to the test surface. After the HA discs, prepared as described above were incubated with the bacteria for three hours, the discs were dipped briefly into Ringer's solution and then transferred to a 12 well plate in which each well contains 1 ml of the previously described dye solution. After a 30 minute incubation at room temperature the discs were transferred to a 12 well plate with containing 1 ml of Ringer's solution in each well and incubated another 15 minutes. The discs were then transferred to well in a 96 well plate to which 200 µl of Ringer's solution had been added. The amount of fluorescence from each disc was measured in a fluorometer using the excitation and emission wavelengths recommended by the Molecular Probes, the manufacturer of the fluorescent dyes. Table 4 present the data obtained from experiments comparing four different commercial mouthwash formulations for their ability to inhibit bacterial adherence to a HA test surface for a 3 hour time period after treatment of a set of HA discs for 3 minutes with each of the mouthwash formulations. The fluorescence data displayed in Table 4 was first corrected by subtracting any background fluorescence due to the test formulations from the raw fluorescence data.

TABLE 4

Bacterial Adherence Assay

| | Relative Fluorescent Units (Average) | Standard Deviation | Percent Adherence to Disc |
|---|---|---|---|
| Ringer's Saline Solution | 2484 | 49 | 100 |
| Mouthwash Placebo | 2458 | 151 | 99 |
| Commercial Mouthwash No. 1 | 1418 | 82 | 57 |
| Commercial Mouthwash No. 2 | 0 | 0 | 0 |
| Commercial Mouthwash No. 3 | 674 | 67 | 27 |
| Commercial Mouthwash No. 4 | 1251 | 88 | 50 |

The results presented in Table 4 demonstrate that the inventive method can be used to determine the relative efficacy of an oral care product in inhibiting or preventing the formation of dental plaque. The data presented in Table 4 show the ability of the different commercial mouthwashes to inhibit bacterial adherence to the HA test surface for 3 hours. Additional tests can easily be performed using the disclosed methods to determine the efficacy of an oral care product for much longer periods.

EXAMPLE 3

Efficacy of a Mouth Rinse in Inhibiting Bacterial Attachment and Growth On an Subzingival Test Surface This example describes a method in accordance with the present invention for measuring the efficacy of oral care products in preventing plaque buildup or otherwise limiting cell attachment and growth in biofilms using a time course method. The preparation of the HA test surfaces and the growth of bacteria are as described in Example 1.

After saliva treatment of a HA disc as described in Example 1, a HA disc is placed into a subgingivally located recess on a tooth prosthesis. In accordance with one embodiment of the present invention, the HA disc is first treated with bacteria for one hour prior to placement in the tooth prosthesis to initiate bacterial binding to the test surface prior to treatment with the mouth rinse. The tooth prosthesis is then placed into a typodont such that the HA disc is located below the typodont gum line. The typodont is placed into a test chamber as described in Example 1.

The tooth prosthesis and HA disc is then treated with a mouth rinse by placing approximately 10 ml of the mouth rinse in the test chamber. The typodont and test surface is then bathed with the mouth rinse using a 25 ml syringe for the time period recommended by the manufacturer of each test mouth rinse. The mouth rinse is then removed from the test chamber and the chamber rinsed twice with Ringer's solution. 5 ml of a log phase bacterial strain (or a mixture of bacterial strains) is added to the test chamber in a solutions consisting of saliva and TSB growth medium such that the fluid level covers the typodont gum-line. The test chamber and typodont is incubated in an orbital shaker (100 RPM) incubator at 37C+5% $CO_2$/air.

At 4 hour intervals the bacterial solutions is removed from the test chamber and the HA disc carefully removed from the tooth prosthesis. Each HA disc is rinsed in a series of 10 ml Ringer's solution baths by gently shaking the discs with forceps to remove excess bacteria, and placed in a 12 well plate containing diluted BacLight Viability Dye (See Example 1) for two hours at room temperature in dark.

The amount of dead and live bacteria attached to each HA disc is measured by first rinsing each disc in Ringer's solution to remove excess dye solution and then placing the disc into a fluorometer to determine amount of fluorescence from each disc. After each measurement the disc is placed back into the typodont for further incubation with a fresh bacteria and saliva solution. One hour later the same disc is again removed from the typodont, stained with the BacLight dyes and fluorescence measured.

A mouth rinse that is highly effective in inhibiting bacterial attachment and growth exhibits an initial low fluorescence emission from the test HA discs. Later measurements of the same disc also show a relatively slow rate of increased fluorescence emission due to a slow bacterial attachment and growth onto the surface of the HA disc. In contrast, a less effective mouth rinse shows a higher amount of fluorescence in the first temporal measurement of fluorescence or a more rapid increase in fluorescence at later time points as compared to an effective mouth rinse.

The embodiments of the invention in which an exclusive property or privilege is claimed are defined as follows:

1. A method for quantitating the efficacy of an oral care product in the removal of a biofilm, the method comprising:
   (a) treating a test surface with saliva;
   (b) binding cells to the test surface to form a biofilm test surface;
   (c) removing cells not bound to the biofilm test surface;
   (d) mounting the biofilm test surface in a tooth prosthesis to form a biofilm tooth prosthesis;
   (e) placing the biofilm tooth prosthesis into a typodont;
   (f) placing the typodont into a collection chamber;
   (g) treating the biofilm tooth prosthesis with an oral care product; and
   (h) quantitatively determining the amount of cells dislodged from the biofilm test surface, said quantitation of cells indicating the efficacy of said oral care product in biofilm removal.

2. A method according to claim 1 further comprising the step of binding one or more additional types of cells to the biofilm test surface.

3. A method according to claim 2 wherein the cells are from a bacterial species found in the mouth.

4. A method according to claim 3 wherein the bacterial species is selected from the group consisting of genera Actinomyces, Bacteroides, Campylobacter, Capnocytophaga, Eikenella, Eubacterium, Fusobacterium, Gemella, Haemophilus, Lactobacillus, Peptostreptococcus, Porphyomonas, Prevotella, Rothia, Selenomonas, Streptococcus, Treponema and Veillonella.

5. A method according to claim 1 wherein the biofilm test surface is mounted in a recess in the tooth prosthesis such that a surface of the bound biofilm test surface is approximately flush to a surface of the tooth prosthesis.

6. A method according to claim 1 wherein the biofilm tooth prosthesis of step (d) is placed into the typodont of step (e) such that the biofilm tooth prosthesis is adjacent to a second tooth prosthesis and the biofilm test surface is facing the interproximal gap between the first and the second tooth prostheses.

7. A method according to claim 1 wherein the biofilm test surface is placed into the tooth prosthesis such that the biofilm test surface is in a subgingival position when the tooth prosthesis is placed into the typodont.

8. A method according to claim 1 further comprising: labeling the cells with one or more fluorescent dyes and quantitatively determining the number of cells dislodged from the biofilm test surface by measuring fluorescence light emitted from the dislodged cells of step (h) of claim 1.

9. A method according to claim 8 wherein the cells bound to the biofilm test surface are labeled with one or more fluorescent dyes prior to placement into the tooth prosthesis.

10. A method according to claim 8 wherein the cells dislodged from the biofilm test surface are labeled with one or more fluorescent dyes after treatment with the oral care product.

11. A method according to claim 8 wherein two fluorescent dyes are used, the first fluorescent dye binding specifically to cells that are alive and the second fluorescent dye binding specifically to cells that are dead.

12. A method according to claim 1 wherein the amount of cells dislodged from the biofilm test surface is quantified using a method comprising:
   (a) preparing a nucleic acid sample from the dislodged cells collected in step (h) of claim 1;
   (b) performing a nucleic acid hybridization reaction on the nucleic acid sample of step (a) with an oligonucleotide primer that hybridizes to nucleic acids isolated from the cells used in step (b) of claim 1; and
   (c) measuring the amount of oligonucleotide primer that hybridizes to the cells nucleic acid sample.

13. A method according to claim 1 wherein the amount of cells dislodged from the biofilm is quantitated using DNA oligonucleotide primers and the polymnerase chain reaction.

14. A method according to claim 1 wherein the amount of cells dislodged from the biofilm test surface is quantitated using an antibody that is reactive to the cells used in step (b) of claim 1.

15. A method according to claim 1 wherein the amount of cells dislodged from the biofilm test surface is quantitated using an assay for a compound found in the cells used in step (b) of claim 1.

16. A method according to claim 1 wherein the amount of cells dislodged from the biofilm test surface is quantitated using a spectrophotometer.

17. A method according to claim 1 wherein the amount of cells dislodged from the biofilm test surface is quantitated by determining the number of colony forming units.

18. A method for quantitating the efficacy of an oral care product in the removal of a biofilm, the method comprising:
   (a) treating a test surface with saliva;
   (b) binding cells to the test surface to form a biofilm test surface;

(c) removing cells not bound to the biofilm test surface;

(d) mounting the biofilm test surface in a tooth prosthesis to form a biofilm tooth prosthesis;

(e) placing the biofilm tooth prosthesis into a typodont;

(f) treating the biofilm tooth prosthesis with an oral care product; and (g) quantitatively determining the amount of cells in the biofilm after completion of step (f), said guantitation of cells indicating the efficacy of said oral care product in biofilm removal.

19. A method according to claim 18 further comprising the step of binding one or more additional types of cells to the biofilm test surface.

20. A method according to claim 19 wherein the cells are from a bacterial species found in the mouth.

21. A method according to claim 19 wherein the bacterial species is selected from the group consisting of genera Actinomyces, Bacteroides, Campylobacter, Capnocytophaga, Eikenella, Eubacterium, Fusobacterium, Gemella, Haemophilus, Lactobacillus, Peptostreptococcus, Porplyromonas, Prevotella, Rothia, Selenomonas, Streptococcus, Treponema and Veillonella.

22. A method according to claim 18 wherein the biofilm test surface is mounted in a recess in the tooth prosthesis such that a surface of the biofilm test surface is approximately flush to a surface of the tooth prosthesis.

23. A method according to claim 18 wherein the biofilm tooth prosthesis of step (d) is placed into the typodont of step (e) such that the biofilm tooth prosthesis is adjacent to a second tooth prosthesis and the biofilm test surface is facing the interproximal gap between the first and the second tooth prostheses.

24. A method according to claim 18 wherein the biofilm test surface is placed into a tooth prosthesis such that the biofilm test surface is in a subgingival position when the tooth prosthesis is placed into the typodont.

25. A method according to claim 18 further comprising: labeling the cells with one or more fluorescent dyes and quantitatively determining the amount of cells in the biofilm test surface after completion of step (f) by measuring fluorescence light emitted from the biofilm test surface.

26. A method according to claim 25 wherein the cells bound to the biofilm test surface are labeled with one or more fluorescent dyes prior to placement into the tooth prosthesis.

27. A method according to claim 25 wherein the cells bound to the biofilm test surface are labeled with one or more fluorescent dyes after treatment with the oral care product.

28. A method according to claim 18 further comprising: labeling the cells with one or more fluorescent dyes prior to treatment of the biofilm tooth prosthesis with an oral care product and quantitatively determining the amount of cells in the biofilm test surface before and after treatment of the biofilm tooth prosthesis with the oral care product by measuring fluorescence light emitted from the biofilm test surface.

29. A method according to claim 18 further comprising: labeling the cells with a first fluorescent dye that only fluoresces when the dye is associated with a live cell and a second fluorescent dye that only fluoresces when the dye is associated with a dead cell and quantitatively determining the amount of live and dead cells in the biofilm test surface by measuring fluorescence light emitted from the biofilm test surface.

30. A method according to claim 29 wherein the fluorescence light emitted from the biofilm test surface is measured in a fluorometer at multiple time intervals after completion of step (f).

31. A method according to claim 18 wherein the amount of cells in the biofilm is quantified using a method comprising:

(a) preparing a nucleic acid sample from the cells in the biofilm test surface after completion of step (f) in claim 18;

(b) performing a nucleic acid hybridization reaction on the nucleic acid sample of step a. with an oligonucleotide primer which hybridizes to nucleic acids isolated from the cells used in step (b) in claim 18; and (c) measuring the amount of oligonucleotide primer that hybridizes to the cell nucleic acid sample.

32. A method according to claim 18 wherein the amount of cells in the biofilm test surface after completion of step (f) is quantitated using DNA oligonucleotide primers and the polymerase chain reaction.

33. A method according to claim 18 wherein the amount of cells in the biofilm test surface is quantitated using an antibody that is reactive to the cells used in step (b) of claim 18.

34. A method according to claim 18 wherein the amount of cells in the biofilm test surface is quantitated using an assay for a compound found in the cells used in step (b) in claim 18.

35. A method for measuring the efficacy of an oral care product in preventing or inhibiting the formation of dental plaque, the method comprising:

(a) treating a test surface with saliva;

(b) binding cells to the test surface to form a biofilm test surface;

(c) mounting the biofilm test surface in a tooth prosthesis to form a biofilm tooth prosthesis;

(d) placing the biofilm tooth prosthesis into a typodont;

(e) treating the test surface with an oral care product;

(f) incubating the test surface with cells under conditions conducive to the formation, of a biofilm on the test surface;

(g) removing cells not bound to the test surface or bound in a biofilm formed on the test surface; and (h) quantitatively determining the amount of cells in the biofilm, said quantitation of cells indicating the efficacy of said oral care product in biofilm removal.

* * * * *

UNITED STATES PATENT AND TRADEMARK OFFICE
CERTIFICATE OF CORRECTION

PATENT NO. : 6,309,835 B1
DATED : October 30, 2001
INVENTOR(S) : L.M. Iyer et al.

It is certified that error appears in the above-identified patent and that said Letters Patent is hereby corrected as shown below:

<u>Title page,</u>
Item [73], Assignee, "Koninkijke" should read -- Koninklijke --
Item [56], References Cited, OTHER PUBLICATIONS, insert -- Ellen, R.P. et al., "In vitro models that Support Adhesion Specificity in Biofilms of Oral Bacteria," Adv Dent Res (11(1):33-42, Apr. 1997). --

<u>Column 16,</u>
Line 3, "Porphyomonas," should read -- Porphyromonas, --
Line 48, "polymnerase" should read -- polymerase --

<u>Column 17,</u>
Line 9, "guantitation" should read -- quantitation --
Line 22, "Porplyromonas," should read -- Porphyromonas, --

<u>Column 18,</u>
Line 49, "formation, of" should read -- formation of --

Signed and Sealed this

Twenty-seventh Day of August, 2002

Attest:

*Attesting Officer*

JAMES E. ROGAN
*Director of the United States Patent and Trademark Office*